United States Patent [19]
Wechter et al.

[11] Patent Number: 5,955,504
[45] Date of Patent: Sep. 21, 1999

[54] COLORECTAL CHEMOPROTECTIVE COMPOSITION AND METHOD OF PREVENTING COLORECTAL CANCER

[75] Inventors: William J. Wechter; John D. McCracken, both of Redlands, Calif.

[73] Assignee: Loma Linda University Medical Center, Loma Linda, Calif.

[21] Appl. No.: 08/402,797

[22] Filed: Mar. 13, 1995

[51] Int. Cl.⁶ .......................... A61K 31/19; A61K 31/40; A61K 31/42

[52] U.S. Cl. .......................... 514/568; 514/569; 514/428; 514/416; 514/375

[58] Field of Search .................................... 514/568, 570, 514/569, 428, 416, 375

[56] References Cited

U.S. PATENT DOCUMENTS

| | | | |
|---|---|---|---|
| 3,755,427 | 8/1973 | Adams et al. | 260/515 A |
| 4,983,765 | 1/1991 | Lukas et al. | 562/401 |
| 5,200,198 | 4/1993 | Geisslinger et al. | 424/489 |
| 5,206,029 | 4/1993 | Brune et al. | 424/489 |
| 5,331,000 | 7/1994 | Young et al. | 514/570 |
| 5,382,591 | 1/1995 | Barberich et al. | 514/413 |
| 5,560,924 | 10/1996 | Wunderlich et al. | 424/451 |

FOREIGN PATENT DOCUMENTS

| | | |
|---|---|---|
| WO 93 16689 | 9/1993 | WIPO . |
| WO 93 24115 | 12/1993 | WIPO . |
| WO 96 28148 | 9/1996 | WIPO . |
| WO 97 48391 | 12/1997 | WIPO . |
| WO 98 09603 | 3/1998 | WIPO . |

OTHER PUBLICATIONS

Hixson et al, Cancer Epidemial, Biomaukeu Prev. (1994) 3(5), 433–8 Abstract Only.

Menzel–Soglowek et al. Agent S T Action, Suddle (1993) 44 23–9 (Abstract Only–original reference to follow in due course.

W.J. Wechter: "Drug Chirality: On the Mechanism of R–Aryl Propionic Acid Class NSAIDs. Epimerization in Humans and the Clinical Implications for the Use of Racemates." J. Clin. Pharmacol., vol. 34, No. 11, 1994, pp. 1036–1042.

W.J. Wechter: "Rac–Flurbiprofen is More Ulcerogenic than its (s)–Enantiomer." Chirality, vol. 5, No. 7, 1993 pp. 492–494.

Moertel, et al., "Levamisole and Fluorouracil for Adjuvant Therapy of Resected Colon Carcinoma," N Engl J Med 1990; 322:352–8.

Heath, et al., "Nonsteroidal Antiinflammatory Drugs and Human Cancer," Cancer, 1994; 74:2885–8.

Marnett, "Aspirin and the Potential Role of Prostaglandins in Colon Cancer," Cancer Research, 1992; 52:5575–89.

Welberg et al., "Proliferation Rate of Colonic Mucosa in Normal Subjects and Patients with Colonic Neoplasms: A Refined Immunohistochemical Method," J Clin Pathol, 1990; 43:453–456.

Thun et al., "Aspirin Use and Reduced Risk of Fatal Colon Cancer," N Engl J Med 1991; 325:1593–6.

Peleg, et al., "Aspirin and Nonsteroidal Anti–inflammatory Drug Use and the Risk of Subsequent Colorectal Cancer," Arch Intern Med. 1994, 154:394–399.

Gridley, et al., "Incidence of Cancer among Patients With Rheumatoid Arthritis" J. Natl Cancer Inst 1993 85:307–311.

Labayle, et al., "Sulindac Causes Regression Of Rectal Polyps In Familial Adenomatous Polyposis" Gastroenterology 1991 101:635–639.

Rigau, et al., "Effects Of Long–Term Sulindac Therapy On Colonic Polyposis" Annals of Internal Medicine 1991 115:952–954.

Giardiello,et al., "Treatment Of Colonic and Rectal Adenomas With Sulindac In Familial Adenomatous Polyposis" N Engl J. Med 1993:328:1313–6.

Pollard, et al., "Effect Of Indomethacin On Intestinal Tumors Induced In Rats By The Acetate Derivative Of Dimethylnitrosamine" Oct. 30, 1981 Science, vol. 214, pp. 558–559.

Reddy, et al., "Inhibitory Effect Of Aspirin On Azoxymethane–Induced Colon Carcinogenesis In F344 Rats" 1993 Carcinogenesis, vol. 14, No. 8 1493–1497.

Gibaldi et al., Pharmacokinetics, 1982, Chapter 1, pp. 1–5.

Jamali, "Pharmacokinetics of Enantiomers of Chiral Non-–steroidal Anti–inflammatory Drugs," Eur. J. Drug Metab. Pharmacokin., 1988, vol. 13, No. 1, pp. 1–9.

Waterhouse, et al., "Aspirin, NSAIDs, and Risk Reduction of Colorectal Cancer", *Arch Intern Med*, vol. 154, Feb. 28, 1994, pp. 366–368.

Lipkin, "Biomakers of Increased Susceptibility to Gastrointestinal Cancer: New Application to Studies of Cancer Prevention in Human Subjects", *Cancer Research* 48, Jan. 15, 1988, pp. 235–245.

*Primary Examiner*—Jerome D. Goldberg
*Attorney, Agent, or Firm*—Knobbe, Martens, Olson & Bear, LLP

[57] ABSTRACT

A composition for use in preventing colorectal cancer and other neoplastic diseases includes an enantiomerically stable R-NSAID or a pharmaceutically acceptable salt thereof in an amount effective to elicit a chemoprotective effect. The composition is substantially free of the S-enantiomer of the R-NSAID. Therapeutic use of the composition is accompanied by reduced adverse side effects.

19 Claims, No Drawings

COLORECTAL CHEMOPROTECTIVE COMPOSITION AND METHOD OF PREVENTING COLORECTAL CANCER

FIELD OF THE INVENTION

The present invention relates to compositions and methods useful in the prevention of colorectal and other gastrointestinal epithelial cancers.

BACKGROUND OF THE INVENTION

Cancer of the colon is common in the western world and is an important cause of morbidity and mortality, having an incidence of about 5% in the U.S. population. As with other types of cancers, cancers of the gastrointestinal tract, including colon cancer, are characterized by abnormal development in cell proliferation and differentiation in the gastrointestinal tract.

The gastrointestinal tract, including the rectum and colon, is lined with epithelial cells which have a high proliferation rate. The lining of the colon, in particular, made up of columnar rows of epithelial cells, is characterized by a series of indentations or crypts. Epithelial cells in the bottom regions of the crypts proliferate and move upward toward the tops of the crypts. In the normal colon, the proliferation region of the large intestine normally occupies the basal or deeper three-quarters of the crypts. A relationship has been observed between the expansion of cell proliferation zones to the upper regions of the crypts and colon cancer. See M. Lipkin, "Biomarkers of Increased Susceptibility to Gastrointestinal Cancer: New Application to Studies of Cancer Prevention in Human Subjects," Cancer Research, Vol. 48, pp. 235–245 (Jan. 15, 1988).

More generally, neoplastic diseases are conditions in which abnormal proliferation of cells results in a mass of tissue called a neoplasm or tumor. Neoplasms have varying degrees of abnormalities in structure and behavior. Some neoplasms are benign while others are malignant or cancerous. An effective treatment of neoplastic disease would be considered a valuable contribution to the search for cancer preventive or curative procedures.

There has been an intensive search for chemoprotective agents for all individuals at risk for colon cancer and other gastrointestinal cancers, particularly individuals over the age of 45. One class of potentially therapeutically useful compounds are the non-steroidal antiinflammatory drugs ("NSAIDs"). NSAIDs, presently in common use as anti-inflammatory agents and as analgesics, are known to have neoplasia chemoprevention and other anti-neoplastic benefits. Physiologically, NSAIDs are known to inhibit the biosynthesis of prostaglandins by the inhibition of the cyclooxygenase enzyme which is ubiquitous in mammalian tissues. See Buckley et al., Drugs, 39(1):86–109 (1990). The role of NSAIDs in prevention of colorectal cancer is discussed in Heath et al., "Nonsteroidal Antiinflammatory Drugs and Human Cancer," Cancer, Vol. 74, No. 10, pp. 2885–2888 (Nov. 15, 1994).

However, the use of NSAIDs in colon cancer prevention has been associated with severe undesirable side effects, which include gastrointestinal, renal and hepatic toxicities, as well as increases in bleeding times due to disruption of platelet function (e.g., thrombocytopenia), and prolongation of gestation due to uterine effects. Another serious side effect associated with the use of certain NSAIDs is leukopenia (decreased white cell count in the blood), and consequent agranulocytosis.

Agranulocytosis is a life-threatening condition that develops very rapidly, and that is difficult to detect even with periodic white-cell counts. The leukopenia/agranulocytosis syndrome has been described for several NSAIDs, such as indomethacin, ketoprofen, and ibuprofen. Indeed, such NSAIDs are contraindicated in patients whose immune systems are compromised by HIV infection, chemotherapy, ionizing irradiation, corticosteroids, immunosuppressives, etc., or by such conditions as emphysema, bronchiectasis, diabetes mellitus, leukemia, burns and the like. A recent review of the adverse effects of NSAIDs is Borda et al., "NSAIDs: A Profile of Adverse Effects," Hanley and Belfus, Inc., Philadelphia, Pa., 1992.

The most recent epidemiologic survey showing that both aspirin and NSAIDs confer protection against colon cancer is Peleg, et al., "Aspirin and Nonsteroidal Anti-inflammatory Drug Use and the Risk of Subsequent Colorectal Cancer," Arch. Intern. Med., Vol. 154, pp. 394–400 (Feb. 28, 1994). This reference identifies a causal relationship between the use of NSAIDs, such as indomethacin, sulindac and peroxicam, and prevention of cancer of the large bowel and rectum. A risk benefit analysis is suggested, however, due to the severe potential gastrointestinal and renal side effects, particularly in the elderly.

The standard treatment for colon cancer currently consists of the administration of a known cancer fighting agent, 5-fluorouracil in combination with the antibiotic levamisole. No improvement in survival among colon cancer patients was shown when 5-fluorouracil was administered alone. The addition of levamisole, which is known to stimulate the immune system and increase T-cell count, showed improved survival rate among these patients. See Moertel et al., "Levamisole and Fluorouracil for Adjuvant Therapy of Resected Colon Carcinoma," N Engl J Med 1990; 322:352–358.

Many NSAIDs exhibit molecular chirality, and thus have R- and S-enantiomers. Such compounds typically are produced as racemic mixtures, which can subsequently be separated into the individual enantiomers.

The enantiomers of several 2-arylpropionic acid NSAIDs are discussed in Yamaguchi et al., Nippo Yakurigaku Zasshi, 90:295–302 (1987). Yamaguchi et al. state that the S-enantiomers of 2-arylpropionic acids have 15–300 times higher prostaglandin synthetase inhibitory activities than the R-enantiomers in the rat.

Caldwell et al., Biochem. Pharmacol. 37: 105–114 (1988) allege that "at best, the R-isomers [of 2-arylpropionic acids] function as prodrugs for the therapeutically active S-forms" when the racemic drug is administered and thus add to both in the therapeutic and toxic effects of the active S-enantiomers. Caldwell et al. further contend that "at worst, the R-enantiomers are undesirable impurities in the active drug" causing difficulties due to non-stereoselective toxicity. The authors indicate that the use of the S-isomers alone should provide safer and more effective use of this class of drugs.

Similarly, it has been generalized that the pharmacokinetics of the enantiomers of 2-arylpropionic acids are different due, at least in part, to the unidirectional metabolic inversion of the R- to the S-enantiomer. However, it has been found that this interconversion depends on the particular compound and the particular species in which it is administered. Jamali, Eur. J. Drug Metabolism Pharmaco. 13: 1–9(1988).

Because of the toxicity and side effects previously described, many NSAIDs are no longer in use in human medicine as analgesics. Some of these NSAIDs include tiaprofenic acid, suprofen, carprofen, pirprofen and indoprofen.

A need has been identified for new formulations of NSAIDs that are effective in treating colorectal and other cancers but are more tolerable with regard to gastrointestinal toxicity. Thus, it would be particularly desirable to provide compositions and methods for the prevention of neoplasia and colorectal cancer but without the aforementioned disadvantages.

SUMMARY OF THE PREFERRED EMBODIMENTS

In accordance with one aspect of the present invention, a composition useful in preventing colorectal cancer includes an enantiomerically stable R-NSAID or a pharmaceutically acceptable salt thereof in an amount effective to elicit a chemoprotective effect. The composition is substantially free of the S-enantiomer of the R-NSAID.

In a preferred embodiment, the R-NSAID is a propionic acid derivative, particularly preferably R-flurbiprofen.

According to another aspect of the present invention, a method of eliciting a colorectal chemoprotective effect in a mammal with reduced gastrointestinal toxicity includes the step of administering to the mammal a composition as described above.

In accordance with still another aspect of the present invention, a method of treating a neoplastic disease in a mammal with reduced gastrointestinal toxicity includes the step of administering to the mammal a composition as described above.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

DETAILED DESCRIPTION OF THE PREFERRED EMBODIMENTS

It has surprisingly been discovered that enantiomerically stable R-isomers of NSAIDs are highly effective in eliciting a colorectal chemoprotective effect, and are also useful in treating neoplastic disease, such as adenocarcinomas including but not limited to colon, rectal and breast cancers. Prophylactic and/or therapeutic administration of compositions including R-NSAIDs in substantially pure form (that is, substantially free of the S-enantiomer of the selected NSAID) is accompanied by a significant reduction in adverse effects associated with the administration of S-enantiomers or racemic mixtures of NSAIDs. Such adverse effects include, but are not limited to, thrombocytopenia and consequent increases in bleeding times; leukopenia and agranulocytosis; prolongation of gestation; gastrointestinal toxicities such as gastric and intestinal ulcerations and erosions; renal toxicities such as papillary necrosis and chronic interstitial nephritis; and hepatic toxicities, such as jaundice, acute hepatitis and hepatic failure.

The term "effective to elicit a chemoprotective effect" as used herein means that abnormal cell proliferation is reduced. A method of measuring cell proliferation in animals is the Labelling Index (LI). Epithelial cells of the distal colon are stained using a histologic biomarker of proliferating cells. Microscopic examination allows for quantification of the proportion of proliferating cells in the crypts. A high proportion of proliferating cells or LI, particularly in the upper portion of the crypts, is an indicator of abnormal cell proliferation. A reduction in the LI of at least 10 to 50%, preferably at least 30% is associated with the reduction of abnormal cell proliferation. Of course, the particular R-NSAID used must be enantiomerically stable in the animal species being tested.

Chemoprevention in man and animals can also be measured by the inhibition of the conversion of the intestinal polyps, in an animal prone to polyposis, to neoplastic or cancerous legions.

A min/+ mouse model can also be used to measure chemopreventive effect. Chemoprevention is achieved in this model if administration of the R-NSAID retards the spontaneous production of intestinal tumors in a min/+ mouse.

Another test of chemoprotection is demonstrated by the prevention of induced tumors in a carcinogen treated mouse or rat.

The inventive compositions comprise at least one enantiomerically stable R-NSAID and are substantially free of the corresponding S-NSAID. As used herein, the term "enantiomerically stable" means that the pharmacokinetic half-life in humans of the interconversion between R- and S-enantiomers is much longer than the elimination half-life from the human body, generally at least three fold and preferably at least ten fold longer.

A suitable measure of the rate of drug elimination from the body is obtained by evaluating data obtained by sampling body plasma, serum or urinary excretion. The rate of change of drug concentration in plasma, for example, is assumed to reflect quantitatively the change in drug concentrations throughout the body. This rate can be approximated by first-order kinetics. See Gibaldi et al. *Pharmacokinetics,* (1982) Chapter 1, pp. 1–5, which is hereby incorporated by reference. The time required for the drug concentration to decrease by one-half is the elimination half-life.

Interconversion from the R-enantiomer to the S-enantiomer of chiral drugs can be evaluated from data available in the literature. A rate equation of $$\ln\left[\frac{[S]}{[R]}\right] = k_i * t$$

is proposed where

[S] and [R] represent the concentrations of the S- and R-enantiomers, respectively, $k_i*$ is the interconversion rate constant, and t is time.

The interconversion half-life is the time at which [R]=[S]/2. Based on the equation above, available data can be evaluated to determine the interconversion half-life for a given species. Calculated values for the interconversion half-life and elimination half-life of some NSAIDs in particular species are presented in Table 1.

TABLE 1

Calculated values for the half life of interconversion for some APA class NSAIDs

| Compound | Interconversion Half-Life (Hours) | Elimination Half-Life (Hours) | Species |
|---|---|---|---|
| Ibuprofen | 2.3 | R.1.4 S1.5 | Rat |
| Ibuprofen | 2.2 | R2.5# | Rat Hepatocytes |
| Ibuprofen | 1.8 | R2.1; S2.2 | Man |
| Ketoprofen | 0.6 | R0.5# | Rat |
| Ketoprofen | 1,(4.6)** | R19.7 S12.4 | Rat |
| Fenoprofen | 0.2 | R0.23# | Ieolated River Rat |

\# estimated from graph(s) in references.
\*\* $t_{1/2}$ in bracket was calculated in range 30–200 min.

Pharmacokinetic data and an explanation of the present state of knowledge for many NSAIDs are presented in Jamali, *"Pharmacokinetics of Enantiomers of Chiral Non-steroidal Anti-inflammatory Drugs," Eur. J. Drug Metab. Pharmacokin.* (1988), Vol. 13, No. 1, pp. 1–9, which is hereby incorporated by reference.

The term "substantially free" indicates that the amount of S-NSAID, if any, present in the composition is insufficient to elicit an adverse effect in the patient to whom the composition is administered or, at most elicits an adverse effect that is tolerable to the patient and is outweighed by the beneficial effect or effects. Preferably, the inventive composition contains at least 90% by weight of a R-NSAID and 10% by weight or less of the corresponding S-NSAID, based upon the total amount of NSAID present in the composition. That is, the ratio of R-NSAID to S-NSAID in the composition is at least about 90:10. Particularly preferably, the inventive composition contains at least 99% by weight of the R-NSAID and 1% or less of the corresponding S-NSAID.

The term "eliciting a colorectal chemoprotective effect" as used herein means relieving, ameliorating or preventing colorectal cancers. Specifically, it means that abnormal cell proliferation in the colon and rectum are reduced. Measurement of these effects are as described above. Again, a reduction in the LI of at least 10 to 50%, preferably at least 30% is associated with the reduction of abnormal cell proliferation.

The chemical structures of NSAIDs vary. Certain NSAIDs, such as ketoprofen and flurbiprofen are arylpropionic acids, while others are cyclized derivatives of arylpropionic acids, arylacetic acids, thiazinecarboxamides, etc.. Depending on the structure of a particular NSAID, the compound may or may not exhibit chirality, i.e, may not have R- and S-enantiomers.

Some of the NSAIDs useful in the present invention are:

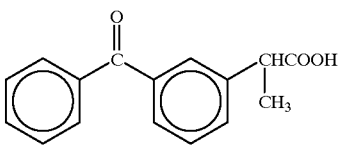

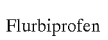
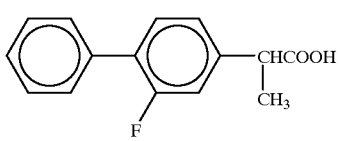

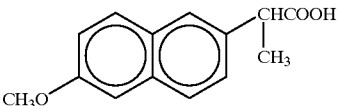

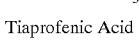
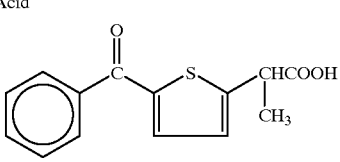

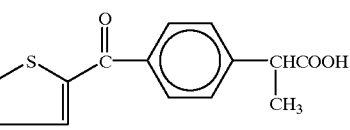

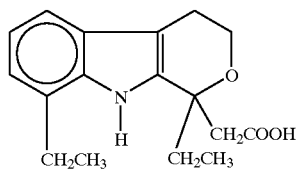

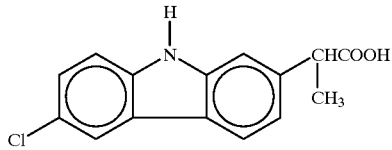

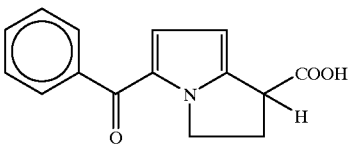

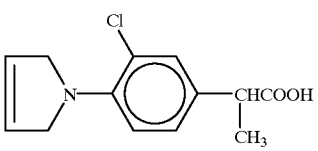

Indoprofen

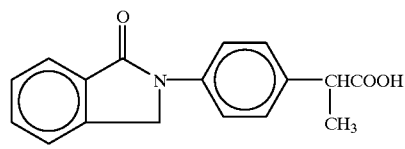

Benoxaprofen

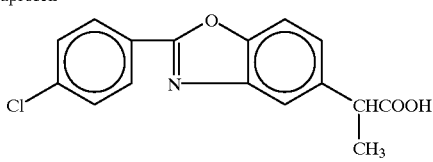

In a preferred embodiment, the R-NSAID employed in the compositions and methods claimed is an arylpropionic acid, in particular a compound selected from the group consisting of R-flurbiprofen, R-ketoprofen, R-naproxen, R-tiaprofenic acid, R-suprofen, R-carprofen, R-pirprofen, R-indoprofen, and R-benoxaprofen. The R-NSAID can also be a cyclized derivative of arylpropionic acid, such as R-ketorolac, or an arylacetic acid, such as R-etodolac. All of these NSAIDs have been used in human medicine in the U.S. and/or Europe as racemates, with the exception of naproxen which is available as the S-isomer only, and are enantiomerically stable. Enantiomerically unstable NSAIDs, for example propionic acid derivatives such as ibuprofen, are not encompassed by the present invention.

Descriptions of specific NSAIDs can be found in various publications. Ketoprofen, for example, is described in U.S. Pat. No. 3,641,127. A description of flurbiprofen is found in U.S. Pat. No. 3,755,427. Ketorolac, another chiral NSAID, is described in U.S. Pat. No. 4,089,969.

A large number of NSAIDs useful according to the invention are commercially available either in the form of racemic mixtures or as optically pure enantiomers. In all cases racemic mixtures contain equal amounts of the R- and S-isomers of the NSAID are provided. For example, the following racemates can be obtained through Sigma Chemical Co.: ketoprofen, flurbiprofen, etodolac, suprofen, carprofen, indoprofen and benoxaprofen. Naproxen, marketed as the S-isomer only, is also available from this source. Additionally, many commercial sources exist for the stereospecific R-isomers of many NSAIDs. R-ketoprofen, R-flurbiprofen and R-ketorolac, for example, are available through Sepracor, Inc.; R-naproxen can be obtained as the sodium salt through Sigma Chemical Co.; R-etodolac is available from Wyeth-Ayerst; R-tiaprofenic acid is available through Roussel (France, Canada, Switzerland, Spain, Denmark, Italy); R-suprofen is manufactured by McNiel Pharmaceuticals; R-carprofen is available from Roche; R-pirprofen is available through Ciba (France, Belgium, Denmark); R-indoprofen can be obtained through Carlo Elba (Italy, U.K.); and R-benoxaprofen is manufactured by Eli Lilly Co.

In addition to commercial sources, racemic mixtures of NSAIDs which are useful according to the invention can be produced by methods described in numerous references and U.S. patents. Synthesis of ketoprofen, for example, is described in U.S. Pat. No. 3,641,127, which is hereby incorporated by reference, while the synthesis of racemic ketorolac is disclosed in Muchowski et al., *J. Med. Chem.*, 28(8):1037–1049 (1985). The optically pure R-isomers of the selected NSAIDs can then be obtained by resolving the racemic mixtures according to well-known methods. See, e.g., U.S. Pat. No. 5,331,000 (R-ketoprofen) and U.S. Pat. No. 5,382,591 (R-ketorolac), the contents of each of which are incorporated herein by reference.

The magnitude of a prophylactic or therapeutic dose of an R-NSAID in the acute or chronic management of cancer or neoplastic disease will vary with the particular NSAID, the severity of the condition to be treated, and the route of administration. The dose and/or the dose frequency will also vary according to the age, body weight, and response of the individual patient.

In general, the total daily dose range for a R-NSAID, for the conditions described herein, is from about 0.1 mg to about 2000 mg, in single or divided doses. Preferably, a daily dose range for cancer prevention should be between about 0.1 mg to about 500 mg in single or divided doses. The preferable daily dose for treatment of neoplastic disease should be about 1.0 mg to about 2000 mg in single or divided doses.

In managing the patient, the therapy should be initiated at a lower dose, perhaps about 0.1 mg to about 100 mg and increased up to about 1000 mg or higher depending on the patient's global response. It is further recommended that infants, children, patients over 65 years, and those with impaired renal or hepatic function, initially receive low doses, and that they be titrated based on individual response(s) and blood level(s).

It may be necessary to use dosages outside these ranges in some cases as will be apparent to those skilled in the art. Further, it is noted that the ordinary skilled clinician or treating physician will know how and when to interrupt, adjust or terminate therapy in consideration of individual patient response.

Any suitable route of administration may be employed for providing the patient with an effective dosage of a R-NSAID. For example, oral, rectal, transdermal, parenteral (subcutaneous, intramuscular, intravenous), intrathecal, and like forms of administration may be employed. Dosage forms include tablets, troches, dispersions, suspensions, solutions, capsules, patches, and the like.

In order to aid in patient compliance with daily dosage requirements, the R-NSAIDs may also be administered by formulating them in a toothpaste. The drug is dissolved in an ethyl alcohol solution and added to the toothpaste so that the final concentration of R-NSAID is from about 0.01 to about 1% on a weight compositions of the present invention basis.

The present method of treatment of colorectal cancer will be enhanced by the use of an R-NSAID as an adjuvant to known chemotherapeutic agents such as 5-fluorouracil and the like.

The pharmaceutical compositions of the present invention comprise an R-NSAID, or a pharmaceutically acceptable salt thereof, as the active ingredient and may also contain a pharmaceutically acceptable carrier, and optionally, other therapeutic ingredients.

The terms "pharmaceutically acceptable salts" or "a pharmaceutically acceptable salt thereof" refer to salts prepared from pharmaceutically acceptable, non-toxic acids or bases. Suitable pharmaceutically acceptable salts include metallic salts, e.g. salts of aluminum, calcium, lithium, magnesium, potassium, sodium and zinc or organic salts, e.g. salts of lysine, N,N'-dibenzylethylenediamine, chloroprocaine, choline, diethanolamine, ethylenediamine, meglumine (N-methylglucamine), procaine and tris.

The term "with reduced gastrointestinal toxicity" as used herein means that the administration of the particular R-NSAID is less ulcerogenic to the gastrointestinal tract of the human or other mammal than the corresponding racemate or S-NSAID. One measure of ulcerogenic activity is the small bowel ulcer score. A rat is treated daily through oral administration of the R-NSAID for 30 days. At the end of the 30 days, the rat is sacrificed and the intestines removed. Lesions of appreciable size in the mucosa are measured. A cumulative score equaling the sum of the diameters of the ulcers measured are reported as the ulcer score. An ulcer score essentially equal to that of a control rat, or a reduction of the ulcer score of at least 50 to 90%, preferably at least 80%, as compared to the corresponding S-NSAID or racemate, is considered a reduction in gastrointestinal toxicity.

The compositions of the present invention can be prepared in any desired form, for example, tablets, powders, capsules, suspensions, solutions, elixirs, and aerosols. Carriers such as starches, sugars, microcrystalline cellulose, diluents, granulating agents, lubricants, binders, disintegrating agents, and the like may be used in the cases of oral solid preparations. Oral solid preparations (such as powders, capsules, and tablets) are preferred over oral liquid preparations. The most preferred oral solid preparations are tablets. If desired, tablets may be coated by standard aqueous or nonaqueous techniques.

In addition to the common dosage forms set out above, the compounds of the present invention may also be administered by controlled release means and/or delivery devices such as those described in U.S. Pat. Nos.: 3,845,770; 3,916,899; 3,536,809; 3,598,123; and 4,008,719, the disclosures of which are hereby incorporated by reference in their entireties.

Pharmaceutical compositions of the present invention suitable for oral administration may be presented as discrete units such as capsules, cachets, or tablets, or aerosol sprays, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the conventional methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more accessary ingredients. Compressed tablets may be prepared by compressing in a suitable machine the active ingredient in a free-flowing form such as powder or granules, optionally mixed with a binder, lubricant, inert diluent, surface active or dispersing agent. Molded tablets may be made by molding, in a suitable machine, a mixture of the powdered compound moistened with an inert liquid diluent. Desirably, each tablet contains from about 0.1 mg to about 1000 mg of the active ingredient, and each cachet or capsule contains from about 0.1 mg to about 600 mg of the active ingredient. Most preferably, the tablet, cachet or capsule contains either one of four dosages, about 0.1 mg, about 50 mg, about 100 mg and about 200 mg of the active ingredient.

The invention is further illustrated by reference to the following examples describing the preparation of some of the compositions of the present invention, as well as their utility. It will be apparent to those skilled in the art that many modifications, both to materials and methods, may be practiced without departing from the purpose and interest of this invention.

EXAMPLE 1

Chemoprotective Effect and Toxicity of R-Flurbiprofen

A study was performed to compare the R- and S-isomers of flurbiprofen with regard to their effect on the Labelling Index (LI) and duodenal ulceration in contrast to the S-isomer.

Female Sprague-Dewley rats were randomized to 4 groups (N=10) receiving 6.3 mg/Kg/day R-flurbiprofen; 6.3 mg/Kg/day S-flurbiprofen; 12.5 mg/Kg/day racemic flurbiprofen; or vehicle control. Fasted rats were sacrificed after 30 days. Small bowel ulcer score was recorded in each group.

The LI is calculated using a histologic biomarker of proliferating cells, a monoclonal antibody to Bromodeoxyuridine (BrD-U). Intestinal crypts are examined microscopically in longitudinal sections such that proliferating cells are identified and quantified as a proportion of total crypt cells. An LI was determined for each rat using BrD-U staining to identify the proportion of mitotic cells in the crypt of Leiberkuhn. Twelve well-oriented crypts (distal colon) were examined in each rat.

The small bowel ulcer score was 0.05; 0.62; 4.54; and 3.22 in the control, R-flurbiprofen, S-flurbiprofen and racemic flurbiprofen groups, respectively. The LI was 12.62 in control animals. The LI was reduced to 8.71 and 9.09 in the R- and S-flurbiprofen treated animals, ($P<0.05$) and further reduced in animals receiving equal-molar doses of both enantiomers.

The results of this study indicate that R-flurbiprofen is much less ulcerogenic than its S-enantiomer, yet suppresses cell proliferation in the distal colon, a chemopreventive effect.

EXAMPLE 2

Toxicity of R-Etodolac

The effects of the isomers of etodolac in the guinea pig are determined as follows. Groups of 6–10 guinea pigs are dosed orally with either vehicle, racemic etodolac (2, 10, 5, 1 and 0.2 mg/kg), S-etodolac (20, 10, 5, 1 and 0.1 mg/kg), or R-etodolac (2, 10, 5, 1 and 0.1 mg/kg). Within 24 hours after the dose, the animals are euthanized and gross abnormalities are recorded in the GI tracts, with particular attention to the gastric mucosa of the stomach. Microerosions and redness (irritations) are noted, and the effects are compared between the treatment groups as described by Abert & Larsson (Acta Pharmacol. Toxicol. 28: 249–257, 1970). Based on such observations, the R-isomer is seen to cause virtually no gastrointestinal irritation.

EXAMPLE 3

Inhibitory Effect on the Activity of Cyclooxygenase

Cyclooxygenase inhibitors (for example aspirin and indomethacin) are known to cause damage and irritation of the gastric mucosa. Assays to determine the inhibitory effect of R-, S- and racemic ketoprofen, reference agents and vehicles on cyclooxygenase activity are conducted using RBL-1 cells (rat basophilic leukemia cell line). The effects of the test compounds, reference agents or vehicles are assessed on the cyclooxygenase-mediated production of $PGF_{2\alpha}$.

RBL-1 cells are grown in culture in Eagle's minimum essential medium supplemented with 12% fetal bovine serum and 1:100 antibiotic/antimycotic mixture at 27° C. Cells are harvested via centrifugation, washed with cold phosphate buffered saline (PBS), and suspended in PBS supplemented with 0.88 μM $CaCl_2$. Cells are incubated in the presence of a screening concentration of test compound or reference agent. Alternatively, cells are incubated in the presence of a vehicle.

Following the incubation period, cyclooxygenase activity is stimulated by the addition of 5 μM of a calcium ionophore to the incubation medium. The reaction is terminated by chilling the tubes on ice.

The cells are then separated via centrifugation, and the supernatant is removed. Aliquots of the supernatant are used to measure the calcium-ionophore-stimulated production of $PGF_{2\alpha}$ via radioimmunoassay.

For each experiment, a vehicle-control is evaluated. A reference standard is also evaluated at a single concentration with each assay.

The results from the aforementioned studies suggest that R-NSAIDs are safe alternatives for chemoprophylaxis in colon cancer. R-NSAIDs suppress cell proliferation in the distal colon, an anti-neoplastic effect.

What is claimed is:

1. A method of treating neoplastic disease with reduced gastrointestinal toxicity in a mammal in need of treatment for said neoplastic disease, comprising
administering to said mammal a composition comprising an enantiomerically stable R-NSAID or a pharmaceutically acceptable salt thereof in an amount effective to elicit a chemoprotective effect, said composition being substantially free of the S-enantiomer of said R-NSAID, wherein said neoplastic disease is sensitive to said composition.

2. A method of claim 1 wherein said neoplastic disease is breast cancer.

3. The method of claim 1 wherein said mammal is a human.

4. The method of claim 1 wherein said R-NSAID is administered orally, transdermally, intravenously or intrathecally.

5. The method of claim 1 wherein the amount of said R-NSAID administered is from 0.1 mg to 2000 mg per day.

6. The method of claim 1 wherein the amount of said composition administered is from 1.0 mg to 2000 mg per day.

7. A method of treating neoplastic disease with reduced gastrointestinal toxicity in a mammal according to claim 1, wherein said R-NSAID is selected from the group consisting of R-flurbiprofen, R-ketoprofen, R-naproxen, R-etodolac, R-ketorolac, R-tiaprofenic acid, R-suprofen, R-carprofen, R-pirprofen, R-indoprofen, and R-benoxaprofen.

8. A method of treating neoplastic disease with reduced gastrointestinal toxicity in a mammal according to claim 7, wherein said R-NSAID is R-flurbiprofen.

9. A method of treating neoplastic disease with reduced gastrointestinal toxicity in a mammal in need of treatment for said neoplastic disease, comprising administering to said mammal a composition comprising:
(a) an enantiomerically stable R-NSAID or a pharmaceutically acceptable salt thereof in an amount effective to elicit a chemoprotective effect, and
(b) a pharmaceutically acceptable carrier,
wherein the ratio of said R-NSAID to its corresponding S-enantiomer in said composition is at least 90:10 by weight; and wherein said neoplastic disease is sensitive to said composition.

10. A method of treating neoplastic disease with reduced gastrointestinal toxicity in a mammal according to claim 9, wherein said composition comprises 25 mg to 2000 mg of said enantiomerically stable R-NSAID, and wherein said R-NSAID is selected from the group consisting of R-ketoprofen, R-flurbiprofen, R-naproxen, R-etodolac, R-ketorolac, R-tiaprofenic acid, R-suprofen, R-carprofen, R-pirprofen, R-indoprofen, and R-benoxaprofen.

11. A method of eliciting a colorectal chemoprotective effect with reduced gastrointestinal toxicity in a mammal in need thereof, comprising administering to said mammal a composition comprising an enantiomerically stable R-NSAID or a pharmaceutically acceptable salt thereof in an amount effective to elicit a chemoprotective effect, said composition being substantially free of the S-enantiomer or said R-NSAID.

12. A method of eliciting a chemoprotective effect with reduced gastrointestinal toxicity in a mammal according to claim 11, wherein said R-NSAID is selected from the group consisting of R-flurbiprofen, R-ketoprofen, R-naproxen, R-etodolac, R-ketorolac, R-tiaprofenic acid, R-suprofen, R-carprofen, R-pirprofen, R-indoprofen, and R-benoxaprofen.

13. A method of eliciting a chemoprotective effect with reduced gastrointestinal toxicity in a mammal according to claim 11, wherein said R-NSAID is R-flurbiprofen.

14. The method of claim 11 wherein said mammal is a human.

15. The method of claim 11 wherein said R-NSAID is administered orally, transdermally, intravenously or intrathecally.

16. The method of claim 11 wherein the amount of said R-NSAID or a pharmaceutically acceptable salt thereof administered is from 0.1 mg to 2000 mg per day.

17. The method of claim 16 wherein the amount administered is from 0.1 mg to 500 mg per day.

18. A method of eliciting a colorectal chemoprotective effect with reduced gastrointestinal toxicity in a mammal in need thereof comprising administering to said mammal a composition comprising:
(a) an enantiomerically stable R-NSAID or a pharmaceutically acceptable salt thereof in an amount effective to elicit a chemoprotective effect, and
(b) a pharmaceutically acceptable carrier,
wherein the ratio of said R-NSAID to its corresponding S-enantiomer in said composition is at least 90:10 by weight.

19. A method of eliciting a chemoprotective effect with reduced gastrointestinal toxicity in a mammal according to claim 18, wherein said composition comprises 25 mg to 2000 mg of said enantiomerically stable R-NSAID, and wherein said R-NSAID is selected from the group consisting of R-ketoprofen, R-flurbiprofen, R-naproxen, R-etodolac, R-ketorolac, R-tiaprofenic acid, R-suprofen, R-carprofen, R-pirprofen, R-indoprofen, and R-benoxaprofen.

* * * * *